United States Patent [19]

Ratton et al.

[11] Patent Number: 4,551,557

[45] Date of Patent: Nov. 5, 1985

[54] BROMINATION OF SUBSTITUTED BENZALDEHYDES

[75] Inventors: Serge Ratton, La Verpilliere; Jean-Luc Bougeois, Sainte-Foy les Lyon, both of France

[73] Assignee: Rhone-Poulenc Specialites Chimiques, Courbevoie, France

[21] Appl. No.: 685,372

[22] Filed: Dec. 24, 1984

[30] Foreign Application Priority Data

Dec. 22, 1983 [FR] France ................................ 83 20797

[51] Int. Cl.⁴ ............................................. C07C 45/63
[52] U.S. Cl. ................................... 568/433; 568/442
[58] Field of Search ............................... 568/433, 437

[56] References Cited

U.S. PATENT DOCUMENTS 4,335,263  6/1982  Minai ................................ 568/437

Primary Examiner—Bernard Helfin
Attorney, Agent, or Firm—Burns, Doane, Swecker & Mathis

[57] ABSTRACT

Substituted bromobenzaldehydes, e.g., 5-bromovanillin, are facilely prepared without conjoint production of HBr, by brominating the corresponding benzaldehydes with a brominating agent couple which comprises hydrobromic acid and a bromide ion oxidizer.

13 Claims, No Drawings

BROMINATION OF SUBSTITUTED BENZALDEHYDES

CROSS-REFERENCE TO RELATED APPLICATION

Our copending application, Ser. No. 685,373, filed concurrently herewith, and assigned to the assignee hereof.

BACKGROUND OF THE INVENTION

1. Field of the Invention

The present invention relates to the preparation of bromobenzaldehydes bearing hydroxy and/or alkoxy substituents, and in particular the compound 5-bromovanillin.

2. Description of the Prior Art

Bromobenzaldehydes bearing hydroxy and/or alkoxy substituents are known to this art as valuable industrial compounds useful as intermediates in various organic syntheses. Thus, 5-bromovanillin (3-bromo-4-hydroxy-5-methoxybenzaldehyde), bromoprotocatechuic aldehyde (3-bromo-4,5-dihydroxybenzaldehyde) and 3-bromo-4,5-dimethoxybenzaldehyde are useful as intermediates in the preparation of 3,4,5-trimethoxybenzaldehyde which is itself an intermediate for the preparation of such pharmaceuticals as trimethoprim 2,4-diamino-5-(3,4,5-trimethoxybenzyl)pyrimidine. These bromobenzaldehydes are also useful in the preparation of bromophenylalanines having hypotensive activity (cf. French Pat. No. 1,592,518).

The alkoxy and/or hydroxy substituted bromobenzaldehydes are typically prepared by reacting bromine with the corresponding aldehyde.

And a variety of methods are known for brominating aromatic aldehydes. Thus, it has been proposed to carry out the bromination of hydroxy and/or alkoxybenzaldehydes in various reaction media. The solvent employed most generally is glacial acetic acid containing, if appropriate, an alkali metal acetate, such as sodium acetate, (cf. Dakin, *Am. Chem. Journal,* 42, 477–98 (1909); Torrey et al, *J. Am. Chem. Soc.,* 31, 583–585 (1909); O. S. Brady et al, *J. Chem. Soc.,* 107, 1858–62 (1915); E. I. Shriner et al, *J. Am. Chem. Soc.,* 51, 2194 (1929); R. A. McIvor et al, *Can. J. of Chem.,* 32, 298–302 (1953); Henry et al, *J. Chem. Soc.,* 2279–89 (1930); F. Misani et al, *J. Org. Chem.,* 10, 356 (1945); R. Pschorr, *Ann,* 391, 23–39 (1912); French Pat. No. 1,592,518). Although this process results in excellent yields of bromobenzaldehydes, particularly in the case of vanillin, it suffers from various disadvantages which make it unattractive from an industrial standpoint. In particular, upon completion of the reaction this process gives rise to a solution of hydrobromic acid in acetic acid from which it is difficult, if not impossible in practice, to recover HBr.

It has also been proposed (cf. R. Pschorr, *loc. cit.*) to replace the glacial acetic acid with chloroform.

In French Pat. No. 72/38,410, published under No. 2,177,693, a process for brominating vanillin has been described, consisting of adding a solution of vanillin in hydrobromic acid, containing 48% by weight of HBr, to bromine.

Lower alcohols, and particularly ethanol, have also been employed as bromination reaction media (cf. F. Tiemann et al, *Ber.,* 7, 615 [1874]). The conjoint formation of irrecoverable methyl bromide or ethyl bromide which may be difficult to justify economically in large-scale production of bromovanillin makes this process unattractive.

In every instance the reaction leads to the formation of one molecule of hydrobromic acid per molecule of bromobenzaldehyde produced in accordance with the following reaction scheme:

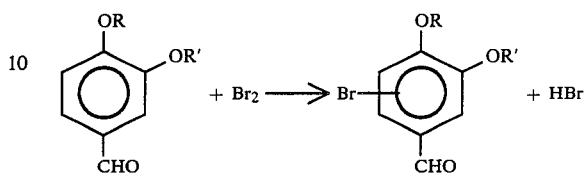

It is found that in such a process only one half of the bromine employed is consumed to form bromobenzaldehydes, with the other half forming hydrobromic acid or, depending upon the solvent employed, alkyl bromides. Recovery and/or economical disposition of these by-products reduce the industrial interest of this process, whatever its application.

From this analysis of the state of the art it follows, therefore, that the conjoint formation of HBr resulting from the use of bromine as a brominating agent presents a serious problem in the industrial application of the known processes.

SUMMARY OF THE INVENTION

Accordingly, a major object of the present invention is the provision of an improved process for the bromination of substituted benzaldehydes, which improved process does not entail the conjoint production of hydrobromic acid, and which otherwise avoids those disadvantages and drawbacks above outlined.

Briefly, the present invention features the preparation of substituted bromobenzaldehydes having the general formula:

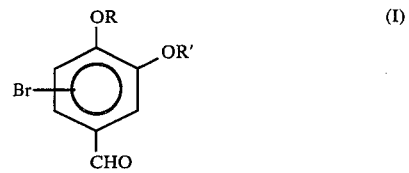

in which R and R' denote a hydrogen atom or a methyl or ethyl radical, and comprising reacting a substituted benzaldehyde of the formula:

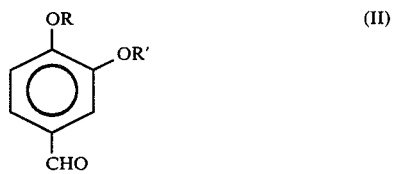

in which R and R' are as defined above, with a brominating agent pair, or couple, which comprises hydrobromic acid and a bromide ion oxidizer.

DETAILED DESCRIPTION OF THE INVENTION

More particularly according to the present invention, exemplary aldehydes of the formula (II) which are advantageously brominated consistent herewith include protocatechuic aldehyde (3,4-dihydroxybenzaldehyde), vanillin, isovanillin (3-hydroxy-4-methoxybenzaldehyde), ethylvanillin, and veratraldehyde (3,4-dimethoxybenzaldehyde).

Protocatechuic aldehyde, vanillin and ethyl-vanillin result in the preparation of the corresponding bromobenzaldehydes containing a bromine atom in the meta-position relative to the aldehyde group and veratraldehyde to 2-bromo-4-hydroxy-3-methoxybenzaldehyde.

Among the oxidizing agents for the conversion of bromide ions to bromine according to the invention, particularly representative are hydrogen peroxide, nitric acid and the hypochlorite ion OCl⁻ preferably employed in the form of alkali metal hypochlorites, such as NaOCl and KOCl. Hydrogen peroxide is the preferred oxidizer for bromide ions; in this event, the reaction may be represented by the following scheme:

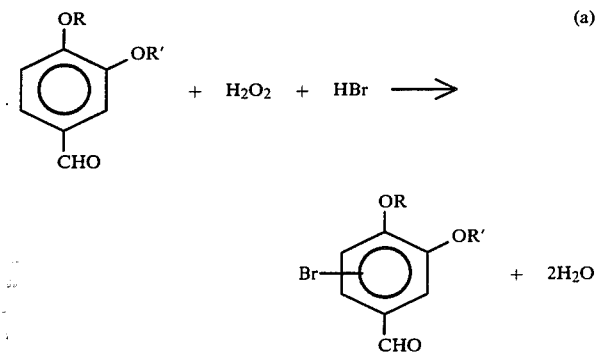

(a)

Although it is generally known to oxidize bromide ions to bromine with the aid of certain oxidizers, the use of the HBr/oxidizer pair to effect bromination of the hydroxy and/or alkoxybenzaldehydes would have been a cause for concern about the course of the oxidation and/or substitution reactions of the starting material. Thus, the prior art teaches that the aldehyde group will be oxidized with hydrogen peroxide according to a reaction of Baeyer and Williger type (cf. C. H. Hassal, *Organic Reactions*, 9, pages 73 to 106 [1957]); J. E. Leffler, *Chem. Rev.*, 45, pages 385 to 410 [1949]). Accordingly, it would not have been expected that the hydroxy and/or alkoxy substituted aromatic aldehydes could be brominated consistent with the reaction mechanism hereof, without concomitant oxidation of the aldehyde functions.

The amount of hydrobromic acid employed in the process according to the present invention may vary over wide limits. In general, the amount of hydrobromic acid expressed in moles per mole of benzaldehyde to be brominated is preferably at least equal to the stoichiometric amount, namely, approximately one mole of HBr per mole of benzaldehyde. An amount less than the stoichiometric amount could of course be employed without departing from the scope of the present invention, but this would be reflected in an incomplete degree of conversion of the benzaldehyde. Beyond this minimum amount, there is no critical upper limit to the amount of hydrobromic acid. In fact, the amount of hydrobromic acid employed depends on the choice of the reaction medium. Thus, when the reaction is carried out in water or an organic compound, it is not essential to use an excess of hydrobromic acid; in this case the amount of HBr may range from 0.8 to 2 moles of HBr per mole of aldehyde, and preferably from 1 to 1.5 mole of HBr. However, it is possible to conduct the reaction in a concentrated aqueous solution of hydrobromic acid which serves as the solvent for the starting material benzaldehyde.

The concentration of the hydrobromic acid employed is also not critical. It essentially depends on matters of practical consideration. When hydrobromic acid is not employed as solvent, the use of dilute acid would contribute to an unnecessary increase in the reaction volume and consequently a lowering in reaction productivity. When hydrobromic acid is employed as the reaction medium, it is preferable that its concentration be sufficient to obtain the highest possible solubility of the starting benzaldehyde so as to avoid either conducting the reaction in a suspension of benzaldehyde or relying on the presence of a third solvent. In this case, use is preferably made of aqueous solutions of HBr containing from 40 to 55% by weight of HBr and preferably from 45 to 50%, which are readily commercially available. However, it would be possible, without departing from the scope of the present invention, to employ dilute aqueous solutions of hydrobromic acid as the reaction medium; the reaction would then take place in a heterogeneous medium on account of the low solubility of the starting material benzaldehydes in dilute hydrobromic acid. Since the bromobenzaldehydes are also insoluble in this medium, a solid mixture of unbrominated benzaldehyde and of bromobenzaldehyde is commensurately formed throughout the progress of the reaction.

The amount of oxidizing agent for the bromide ions, expressed in moles per mole of aldehyde, obviously depends upon the nature of the particular oxidizing agent in question. Thus, when the oxidizing agent is hydrogen peroxide, this amount is preferably close to the stoichiometry of the reaction represented by the scheme (a), that is to say, approximately 1 mole per mole of aldehyde. Although up to 2 moles of $H_2O_2$ may be employed per mole of aldehyde without difficulty, this does not entail any particular advantage. In practice, the amount of $H_2O_2$ advantageously ranges from 0.8 to 1.5 mole per mole of aldehyde. The use of too great a deficiency of hydrogen peroxide would give rise to a reduction in the degree of conversion of the aldehyde. When hydrobromic acid is not employed as the reaction medium, but as a simple bromine carrier, it is preferable that there be an excess of HBr relative to hydrogen peroxide; this excess may be on the order of 0.01 to 0.5 mole of HBr per mole of hydrogen peroxide employed. When nitric acid is employed as oxidizer, the overall reaction may be represented by the following scheme:

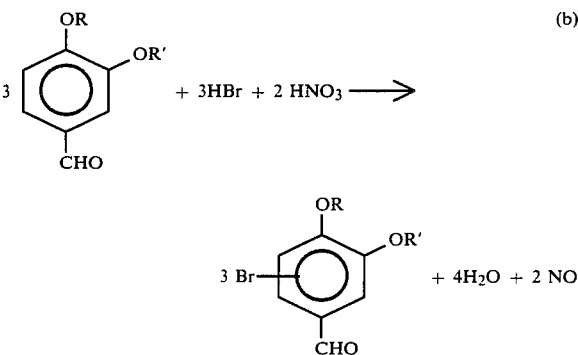

(b)

In this instance, the amount of nitric acid expressed in moles of $HNO_3$ per mole of benzaldehyde may be close to the stoichiometry of the reaction, namely, # of a mole per mole of benzaldehyde, or may be slightly different from this value. In practice, the amount of nitric acid may vary from 0.35 to 1 mole per mole of benzaldehyde and preferably from 0.6 to 0.8 mole per mole of HBr.

The concentration of nitric acid is also not critical and depends upon practical aspects related to process productivity and to the commercial availability of aqueous solutions of $HNO_3$. In general, aqueous solutions containing from 20 to 75% by weight of $HNO_3$ are used.

It has been found that it is preferable to employ, jointly with the nitric acid, nitrous acid which promotes a rapid starting of the reaction. In this instance, it is practical to use an alkali metal nitrite (sodium or potassium nitrite) to initiate the reaction. An amount on the order of 0.01 mole of nitrite per mole of aldehyde is generally sufficient to initiate the reaction; it is unnecessary for such amount to be greater than 0.2 mole per mole of aldehyde. An amount of 0.05 to 0.15 mole is satisfactory.

When the hypochlorite ion is used as oxidizer, it is employed in the form of an aqueous solution of an alkali metal hypochlorite such as sodium and potassium hypochlorites. In practice, aqueous solutions of sodium hypochlorite are used, the concentration of which is not critical but selected as a function of the same practical factors as those referred to in the case of the other oxidizers. The amount of hypochlorite expressed in moles per mole of benzaldehyde is close to the stoichiometry of the reaction represented by the reaction scheme:

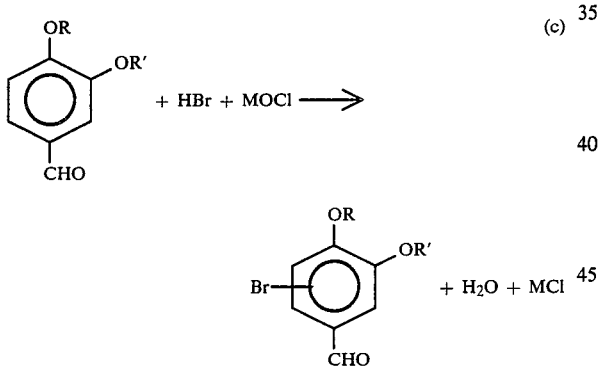

in which M denotes an alkali metal; namely, approximately 1 mole per mole of benzaldehyde. In general, an amount of hypochlorite ranging from 0.8 to 1.5 mole per mole of benzaldehyde is suitable, although it is possible to operate outside these limits without departing from the scope of the invention. Here again, it is preferable to conduct the reaction in the presence of an excess of hydrobromic acid relative to the stoichiometric amount of hypochlorite when hydrobromic acid is not employed as the reaction medium. This excess may be on the order of 0.01 mole to 0.5 mole relative to the stoichiometric amount.

When a third organic compound is employed as the reaction medium, any compound which is inert towards the hydrobromic acid/oxidizer pair or its components may be used. Preferably, solvents for benzaldehydes are used. The lower halogenated aliphatic hydrocarbons (containing from 1 to 4 carbon atoms), aliphatic acids, and lower aliphatic ethers are particularly highly suitable; specific examples of such preferred compounds are chloroform, anhydrous acetic acid, anhydrous propionic acid, and isopropyl ether.

It is of course also within the ambit of the invention to combine two or more organic solvents or an organic solvent and an aqueous solution of hydrobromic acid as the reaction medium. When a carboxylic acid is employed as solvent, the hydrobromic acid required for the reaction to take place may be generated in situ by charging an alkali metal bromide (for example, sodium bromide).

The concentration of aromatic aldehyde in the reaction medium too is not critical and can vary over wide limits. Its selection depends upon practical considerations which are well known to this art. It must provide the best possible compromise between the stirrability of the reaction medium and the productivity of the apparatus used.

The temperature at which the reaction is carried out may also vary over wide limits. Generally a temperature of 0° to 100° C. is suitable. Preferably, the operation is carried out in a temperature range from 5° to 60° C.

A preferred embodiment of the invention consists of dissolving the aromatic aldehyde to be brominated in an aqueous solution of hydrobromic acid of a concentration of from 40 to 55% by weight (preferably from 45 to 50% by weight), then contacting this solution with a solution of hydrogen peroxide at a suitable temperature. The bromobenzaldehyde resulting from the reaction precipitates as it is formed. Upon completion of the reaction it suffices to isolate this product by filtration and to wash it with hydrobromic acid. The filtrate and the acid wash containing unconverted aldehyde, in this case, are advantageously cycled to a new bromination operation. Such a process is most particularly suitable for the preparation of bromobenzaldehydes having the general formula:

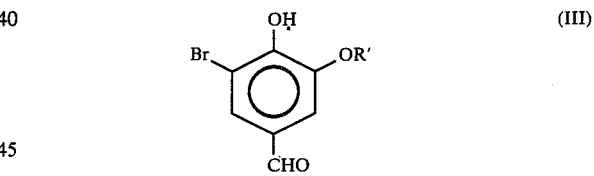

in which R' is as defined above, and particularly for the preparation of 5-bromovanillin.

The process according to the invention is particularly highly suitable for continuous operation.

In order to further illustrate the present invention and the advantages thereof, the following specific examples are given, it being understood that same are intended only as illustrative and in nowise limitative.

EXAMPLE 1

Vanillin (15.2 g; 0.1 mole) was dissolved at ambient temperature in HBr at a concentration of 48% by weight (180 ml) in a 500 ml round glass flask equipped with a stirring system, thermometer, a dropping funnel and cooled with a cold water bath. The mixture was cooled to approximately 5° C. $H_2O_2$ at a concentration of 30% by weight (11.4 g; 0.1 mole) was then added dropwise. The solution, which turned red in color where the $H_2O_2$ dropped into the mixture, became colorless in a few seconds. The reaction mass became heterogeneous very quickly. When the addition was complete the mixture was maintained under stirring for 6 hours at 5° C., after which ice water (150 ml) was added to the reaction mixture. The precipitate was filtered off and washed on the filter with ice water.

After drying under vacuum at approximately 60° C., a dry precipitate was obtained which weighed 21.28 g and had a melting point of 160° C. The composition, determined by high pressure liquid chromatography, was 95% 5-bromovanillin and 3% vanillin.

The results obtained were as follows:
Degree of conversion of vanillin: 96.2%
Yield of 5-bromovanillin/vanillin converted: 91.1%
Yield of 5-bromovanillin/vanillin employed: 87.6%.

EXAMPLE 2

The procedure of Example 1 was repeated, but 70 ml of hydrobromic acid were employed instead of 180 ml. The reaction medium was heterogeneous, the vanillin being incompletely dissolved. The results obtained were the same as in Example 1.

EXAMPLE 3

Vanillin (15.2 g) was added at ambient temperature to hydrobromic acid at a concentration of 47% by weight (100 ml). Hydrogen peroxide in the form of a solution containing 30% by weight (i.e., 14.73 g; 0.13 mole) was added dropwise to the suspension thus produced. The temperature gradually increased to 30° C.

When the addition was complete the contents of the flask were maintained for 10 minutes at 30° C. and then the reaction mixture was treated as in Example 1. The filtrate was extracted with chloroform (3 × 100 ml). The chloroform extract was evaporated to dryness and the residue mixed with the solid collected by filtering. The entire mass was dried to constant weight and then vanillin and bromovanillin were determined as in Example 1.

The results obtained were as follows:
Degree of conversion of vanillin: 86.1%
Yield of 5-bromovanillin/vanillin converted: 96.7%

EXAMPLE 4

The procedure of Example 3 was repeated, with hydrobromic acid at a concentration of 47% by weight being replaced by 3 N hydrobromic acid (180 ml) and 0.11 mole of hydrogen peroxide being used.

The results obtained were as follows:
Degree of conversion of vanillin: 86.1%
Yield of 5-bromovanillin/vanillin converted: 96.7%

EXAMPLE 5

The procedure of Example 4 was repeated, but with hydrobromic acid at a concentration of 47% by weight being replaced by 2 N hydrobromic acid (50 ml) and chloroform (100 ml) and the hydrogen peroxide by nitric acid (1.81 g of an aqueous solution containing 65% by weight; 0.0187 mole) and sodium nitrite (0.01 mole).

The results obtained were as follows:
Degree of conversion of vanillin: 40.3%
Yield of 5-bromovanillin/vanillin converted: 58%

While this invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of a substituted bromobenzaldehyde having the general formula:

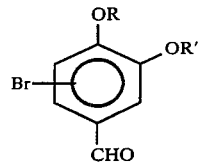

(I)

wherein R and R' are each hydrogen, methyl or ethyl, comprising brominating a substituted benzaldehyde having the general formula:

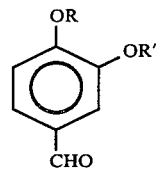

(II)

wherein R and R' are as defined above, with a brominating agent couple which comprises hydrobromic acid and a bromide ion oxidizer.

2. The process as defined by claim 1, wherein said bromide ion oxidizer comprises hydrogen peroxide, nitric acid or analkali metal hypochlorite.

3. The process as defined by claim 1, wherein the amount of hydrobromic acid comprising said brominating agent couple is at least 0.8 mole per mole of the benzaldehyde (II).

4. The process as defined by claim 1, wherein said brominating agent couple comprises hydrogen peroxide or an alkali metal hypochlorite, the amount thereof ranging from 0.8 to 1.5 mole per mole of the benzaldehyde (II).

5. The process as defined by claim 1, wherein said brominating agent couple comprises nitric acid, the amount thereof ranging from 0.35 to 1 mole of HNO₃ per mole of the benzaldehyde (II).

6. The process as defined by claim 5, wherein said brominating agent couple further comprises from 0.01 to 0.2 mole of nitrous acid per mole of benzaldehyde (II).

7. The process as defined by claim 1, said bromination being carried out in a concentrated solution of hydrobromic acid.

8. The process as defined by claim 7, wherein said hydrobromic acid is at a concentration of 45 to 60% by weight.

9. The process as defined by claim 1, said bromination being carried out in an organic solvent for the benzaldehyde (II).

10. The process as defined by claim 9, wherein said organic solvent comprises a lower alkanoic acid, halogenated aliphatic hydrocarbon or lower aliphatic ether.

11. The process as defined by claim 1, wherein said bromination is carried out at a temperature of from 0° to 100° C.

12. The process as defined by claim 1, wherein said benzaldehyde (II) comprises protocatechuic aldehyde, vanillin, isovanillin, ethylvanillin or veratraldehyde.

13. The process as defined by claim 1, wherein said bromobenzaldehyde (I) comprises 5-bromovanillin.

* * * * *